United States Patent [19]

Sleeter et al.

[11] 4,211,107
[45] Jul. 8, 1980

[54] PIPE TESTING MACHINE WITH CLAMPING PRESSURE KEYED TO HYDROSTATIC TEST PRESSURE

[75] Inventors: Michael R. Sleeter, Millbury, Ohio; James C. Dehring, Tecumseh, Mich.

[73] Assignee: Owens-Corning Fiberglas Corporation, Toledo, Ohio

[21] Appl. No.: 759,619

[22] Filed: Jan. 17, 1977

[51] Int. Cl.² .......................................... G01M 3/04
[52] U.S. Cl. ................................................. 73/49.6
[58] Field of Search ...................... 73/49.6, 49.5, 49.1

[56] References Cited

U.S. PATENT DOCUMENTS

| 1,423,902 | 7/1922 | Bauer et al. | 73/40 |
| 2,705,888 | 4/1955 | Sedgwick | 73/49.6 |
| 2,907,202 | 10/1959 | McConnell | 73/49.6 |
| 3,312,103 | 4/1967 | Goeke | 73/49.6 |
| 3,350,921 | 11/1967 | Brauer | 73/49.6 |

FOREIGN PATENT DOCUMENTS 1091243  11/1967  United Kingdom .................... 73/49.6

*Primary Examiner*—S. Clement Swisher
*Attorney, Agent, or Firm*—Ronald C. Hudgens; Paul J. Rose; Patrick P. Pacella

[57] ABSTRACT

A pipe testing machine wherein clamping pressure on the ends of a plastic pipe being tested under internal water pressure is maintained proportional to the internal pressure so as not to crush the ends of the pipe.

7 Claims, 3 Drawing Figures

PIPE TESTING MACHINE WITH CLAMPING PRESSURE KEYED TO HYDROSTATIC TEST PRESSURE

In a machine for hydrostatically testing reinforced plastic pipe of relatively large diameter, a certain clamping force against the open ends of the pipe is required to seal the ends when the pipe contains water at zero gauge pressure. Additional clamping force is required to oppose the force generated by increasing the internal water pressure to the maximum test pressure. Should the maximum clamping force be applied before the internal pressure in the pipe is increased from zero gauge pressure, or if the internal pressure is released suddenly from maximum test pressure to zero gauge pressure while the maximum clamping force is applied, the machine is likely to crush the ends of the pipe. An object of the invention is to provide a pipe testing machine having an automatic control system preventing crushing of the pipe.

Figure 1:
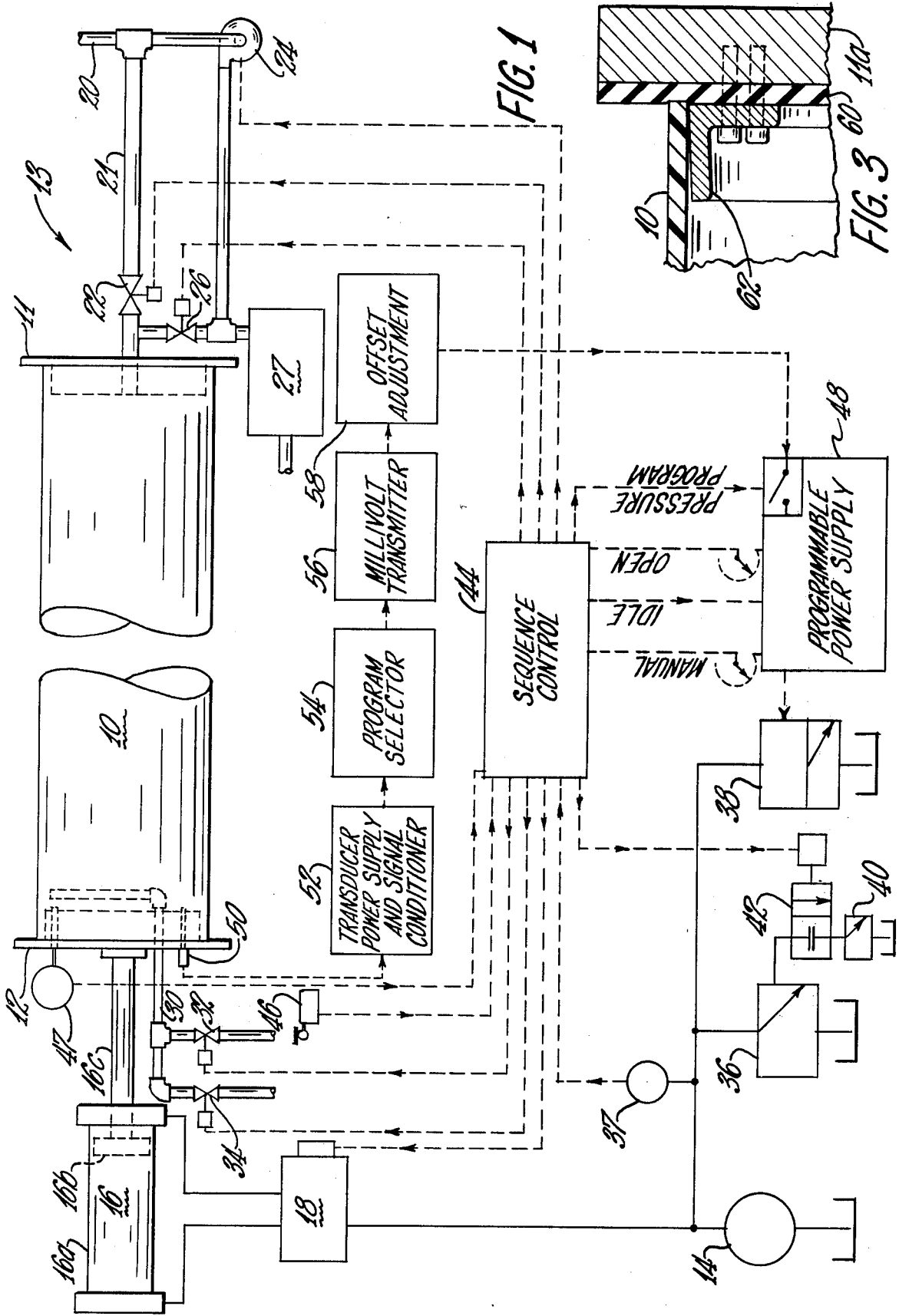
Figure 2:
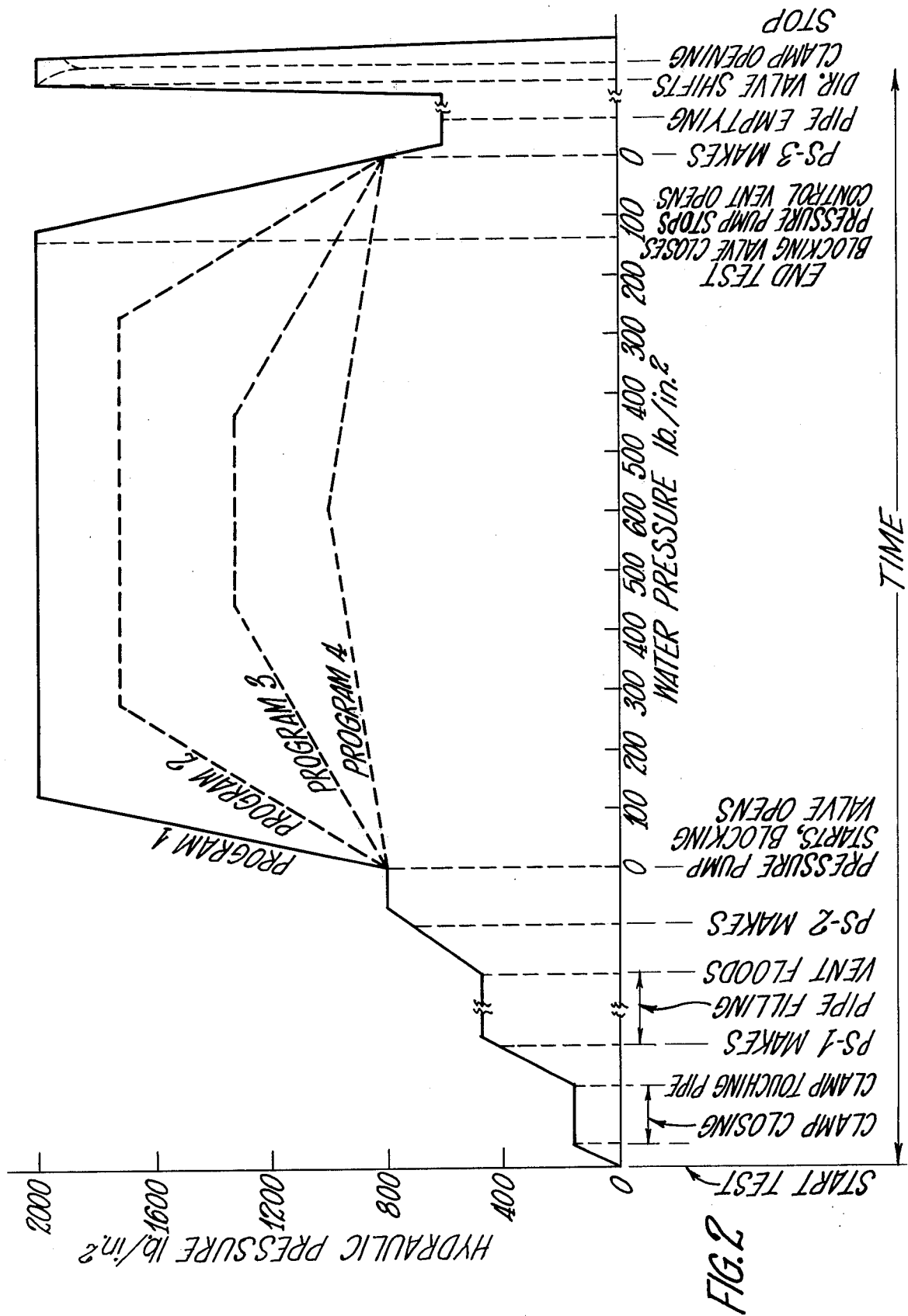

In the drawings, FIG. 1 is a schematic diagram illustrating the control system of the invention;

FIG. 2 is a time-pressure graph illustrating testing cycles for pipes of various diameters; and FIG. 3 is a fragmentary sectional view of an end of a pipe and the adjacent clamp of the testing machine.

With respect to the drawings, a pipe 10 is shown in FIG. 1 clamped between a stationary clamping plate 11 and a movable clamping plate 12 of a hydrostatic pipe testing machine 13. A constant displacement pump 14 supplies hydraulic fluid such as oil to a hydraulic actuator 16 through a directional control valve 18. The actuator 16 includes a cylinder 16a, a piston 16b reciprocable therein, and a piston rod 16c connected at one end to the piston 16b and at the other end to the movable clamping plate 12.

A water supply pipe 20 is connected to an inlet pipe 21 leading through the stationary clamping plate 11 to the inside of the pipe 10 and having an electrically operable valve 22 therein. The supply pipe 20 is also connected to a pressure pump 24 having its outlet connected to the pipe 21 downstream of the valve 22 under the control of an electrically operable valve 26. The pressure of the water supplied to the pipe 10 by the pump 24 is controlled by an adjustable relief valve or pressure regulator 27 also connected to the outlet of the pump. A vent pipe 30 extends through the movable clamping plate 12 for venting water from the pipe 10 either under the control of an electrically operable primary vent valve 32 or under the control of an electrically operable controlled vent valve 34 having a variable orifice.

The outlet from the hydraulic fluid pump 14 is also connected to a manually adjustable high pressure relief valve 36, to a pressure switch 37 having two sets of contacts operable at different pressures, and to an electrically adjustable relief or modulating valve 38. The relief valve 36 is provided with a manually adjustable pilot relief valve 40 controlled by an electrically operable valve 42.

The machine 13 is provided with electrical controls including a sequence control means 44 comprising various switches and relays and connected to the control valve 42, the pressure switch 37, the directional control valve 18, the controlled vent valve 34, the primary vent valve 32, a suitable mounted flow controlled limit switch 46 subject to pressure of water discharged through the primary vent valve 32, a reverse pressure switch 47 mounted on the movable clamping plate 12 and subject to water pressure in the pipe 10, the water supply valve 22, the pump pressure water supply valve 26, the pump 24, and also in four different modes to a programmable power supply 48 for the electrically adjustable relief or modulating valve 38.

The electrical controls also include a pressure transducer 50 mounted on the movable clamping plate 12 and subject to the water pressure in the pipe 10. The transducer 50 is connected to a power supply and signal conditioner means 52 which supplies the transducer with power and converts the pressure signal to a level that can be used to establish a circuit in a program selector 54 connected thereto and comprising four voltage dividers used selectively one at a time in accordance with the diameter of the pipe being tested. The program selector 54 is connected to a millivolt transmitter or amplifier 56 which converts the signal from the program selector into a signal compatible to the input of the programmable power supply 48 for the modulating valve 38. The millivolt transmitter 56 is connected to the programmable power supply 48 through an offset adjustment means 58. The sequence control means 44 determines which input to the programmable power supply 48 produces the output to the modulating valve 38.

FIG. 3 shows the preferred construction of the clamping plate 11 of FIG. 1. A relatively thick metal plate 11a is covered on the side thereof facing the pipe 10 with a rubber disc 60. A tubular member 62 fitting inside the pipe 10 has an internal flange suitably removably secured to the plate 11a as by screws. Different sizes of tubular members such as the member 62 are provided for pipe of different diameters.

OPERATION

With the hydraulic fluid pump 14 running, the program selector 54 adjusted for the diameter of the pipe, the test pressure set on the relief valve 27, and the pipe 10 suspended in place between the clamping plates 11 and 12, a "START TEST" pushbutton (not shown) is depressed to cause the sequence control means 44 to shift the directional control valve 18 to clamping position to feed hydraulic fluid to the left-hand end of the cylinder 16a as viewed in FIG. 1. The sequence control means 44 opens the control valve 42 at the same time the directional control valve 18 is shifted to clamping position, thus placing the hydraulic pressure under the control of the pilot relief valve 40, which for example may be set at 475 pounds per square inch (p.s.i.). As the cylinder 16a is filling and the piston 16b is moved to the right, but before the clamping plate 12 engages the pipe 10, the hydraulic pressure probably does not exceed 200 p.s.i. When the clamping plate 12 engages the pipe at one end and the other end is in engagement with the clamping plate 11, the flow of hydraulic fluid to the cylinder 16a ends, but the hydraulic pressure builds up to the setting of the relief valve 40. The low pressure set of contacts of the pressure switch 37 closes, for example at 400 p.s.i., signaling the sequence control means 44 that the clamping plate 12 has engaged the pipe 10 with sufficient force to seal the ends against the rubber discs such as the disc 60. The sequence control means 44 then opens the water supply valve 22 and the primary vent valve 32. The pipe 10 fills with water until the level reaches the top of the vent pipe 30. Water then flows through the vent valve 32 and closes the limit switch 46, signaling the sequence control means 44 that the pipe 10 is substantially full. The sequence control means 44 up to this time has, through the "idle" signal to the programmable power supply 48, been directing the modulating valve 38 to operate, for example, at 600 p.s.i. When the limit switch 46 closes, the sequence control means directs the programmable power supply 48 to look for its reference at the incoming water pressure signal from the pressure transducer 50, which signal passes through the signal conditioner 52, the program selector 54, the millivolt transmitter 56, and the offset adjustment means 58 before entering the programmable power supply 48. The offset adjustment means 58 may, for example, be set to provide a base offset equivalent to a controlling pressure of 800 p.s.i. for the modulating valve 38. Thus, when the limit switch 46 closes and the sequence control means 44 changes the signal to the programmable power supply 48 from "idle" (600 p.s.i.) to "pressure program", and the gauge pressure in the pipe 10 is substantially zero, the signal from the pressure transducer 50, after going through offset adjustment means 58, will be directing the programmable power supply 48 to adjust the relief setting of the modulating valve 38 to 800 p.s.i. Then, as the pressure in the pipe 10 is increased for the test, the signal from the pressure transducer 50 will increase and direct the programmable power supply 48 to increase the relief setting of the modulating valve 38 proportionately above 800 p.s.i.

When the limit switch 46 closes, the sequence control means 44 also closes the control valve 42 and cuts off the pilot relief valve 40. The high pressure relief valve 36 may be set, for example, to open at 2100 p.s.i. Therefore, when the control valve 42 closes, the control of the clamping pressure is shifted to the modulating valve 38. As the hydraulic clamping pressure increases from the 475 p.s.i. setting of the pilot relief valve 40 toward the 800 p.s.i. base setting of the modulating valve 38, the high pressure set of contacts of the pressure switch 37 closes, for example at 750 p.s.i., verifying to the sequence control means 44 that the programmable power supply 48 has shifted from the "idle" to "pressure program" mode and that control valve 42 has closed. The sequence control means 44 then closes the water supply valve 22, opens the water pump valve 26, starts the water pressure pump 24, and closes the primary vent valve 32. The closing of the vent valve 32 allows the limit switch 46 to open. As the water pressure inside the pipe 10 increases, the reverse pressure switch 47 opens, for example at 10 p.s.i. The water pressure increases to the test pressure determined by the setting of the relief valve 27 and the hydraulic clamping pressure on the pipe 10 increases accordingly under the control of the pressure transducer 50, programmable power supply 48, and modulating valve 38, and in accordance with the selected setting of the program selector 54. The plastic pipe expands slightly under the internal pressure.

To end a test, an "END TEST" pushbutton (not shown) is depressed, causing the sequence control means 44 to close the water pump valve 26 and trap the water in the pipe 10 at the test pressure with the pipe in the slightly expanded condition. Then the sequence control means 44 stops the water pump 24 and opens the controlled vent valve 34. While the pipe 10 contracts from its slightly expanded condition back to its normal condition, the variable orifice of the controlled vent valve 34 allows the water in the pipe 10 to escape gradually and the pressure to decline sufficiently slowly to enable the hydraulic clamping pressure to be proportionately reduced therewith under the control of the sensing pressure transducer 50, programmable power supply 48, and modulating valve 38. When the water pressure has decreased to the 10 p.s.i. setting of the reverse pressure switch 47, the switch 47 closes and the sequence control means 44 closes the controlled vent valve 34, shifts the programmable power supply 48 to its "idle" mode from the "pressure program" mode of operation, thus effecting control of the modulating valve 38 at 600 p.s.i., opens a drain valve (not shown) connected to the pipe 10 through the clamping plate 11, and opens the primary vent valve 32 to allow free flow of air into the pipe 10 to displace the exiting water. After a predetermined time, the sequence control means 44 shifts the programmable power supply 48 from its "idle" to the "open" mode of operation, wherein it directs the modulating valve to operate, for example, at 2000 p.s.i., shifts the directional control valve 18 to clamp opening position, and closes the primary vent valve 32 and the drain valve (not shown). After the clamping plate 12 has been retracted out of the pipe 10 by the piston 16b, it closes a limit switch (not shown) which signals the sequence control means 44 to shift the directional control valve 18 to a neutral position and to shift the programmable power supply 48 from its "open" to the "idle" mode of operation.

The test cycle is illustrated in FIG. 2, wherein "clamp" means the movable clamping plate 12, "PS-1" means the low pressure set of contacts of the pressure switch 37, "vent" means the vent pipe 30, "PS-2" means the high pressure set of contacts of the pressure switch 37, "pressure pump" means the water pressure pump 24, "blocking valve" means the water pump valve 26, "control vent" means the controlled vent valve 34, and "PS-3" means the reverse pressure switch 47. Programs 1, 2, 3 and 4 of the program selector 54 are for pipes of successively decreasing diameter. As shown, for program 1, the pipe can be tested to a water pressure of about 125 p.s.i. with a clamping pressure in the cylinder 16a of about 2000 p.s.i. The higher water test pressures for programs 2, 3, and 4 are accomplished with lower unit clamping pressures because of the reduced cross sectional areas of pipe to be clamped.

Various modifications may be made in the testing machine shown and described without deporting from the spirit and scope of the invention.

We claim:

1. A pipe testing machine comprising a pair of spaced clamping plates, means for applying clamping pressure to the clamping plates to seal opposite ends of a test pipe against internal test pressure, means for subjecting the test pipe to internal fluid pressure, means for continuously sensing the magnitude of the internal pressure in the pipe and providing an electrical signal varying in magnitude in accordance with the magnitude of the internal pressure in the pipe, and electrically adjustable modulating valve means for receiving the electrical signal and proportioning the clamping pressure to the sensed internal pressure.

2. A pipe testing machine as claimed in claim 1 including means for releasing the internal test pressure and wherein the proportioning means is effective while the pressures are decreasing.

3. A pipe testing machine as claimed in claim 1 wherein the means for subjecting the test pipe to internal fluid pressure comprises means for introducing water into the pipe and means for pressurizing the water in the pipe after the pipe is full.

4. A pipe testing machine as claimed in claim 1 wherein the clamping pressure is supplied by hydraulic actuator and pump means.

5. A pipe testing machine comprising a pair of spaced clamping plates, hydraulic actuating means for moving one of the clamping plates selectively toward and away from the other for respectively clamping and unclamping a pipe therebetween at opposite ends, hydraulic pumping means for supplying hydraulic fluid under pressure to the actuating means to seal the ends of the pipe, means for filling the clamped pipe with water through one of the clamping plates, means for increasing the water pressure in the pipe to test the pipe, means for continuously sensing the magnitude of the water pressure in the pipe and providing an electrical signal varying in magnitude in accordance with the magnitude of the water pressure in the pipe, and electrically adjustable modulating valve means for receiving the electrical signal and proportioning the hydraulic fluid pressure in the actuating means to the sensed magnitude of the water pressure.

6. A pipe testing machine as claimed in claim 5 wherein a plastic test pipe expands under the water pressure therein and the machine includes controlled vent valve means for gradually releasing water from the expanded pipe and permitting the water pressure in the pipe to decrease sufficiently slowly to enable the hydraulic fluid pressure in the actuating means to be reduced proportionately therewith under the control of the water pressure sensing means and modulating valve means while the expanded pipe contracts back to its normal condition.

7. A pipe testing machine comprising a pair of spaced clamping plates, means for applying clamping pressure to the clamping plates to seal opposite ends of a test pipe against internal test pressure, means for subjecting the test pipe to internal fluid pressure, means for continuously sensing the magnitude of the internal pressure in the pipe and providing an electrical signal varying in magnitude in accordance with the magnitude of the internal pressure in the pipe, and electrically adjustable modulating means for receiving the electrical signal and proportioning the clamping pressure to the sensed internal pressure.

* * * * *